United States Patent [19]

Masukawa et al.

[11] Patent Number: 5,017,467
[45] Date of Patent: May 21, 1991

[54] PHOTOGRAPHIC MATERIAL WITH IMIDAZOLE CYAN COUPLER

[75] Inventors: Toyoaki Masukawa; Noritaka Nakayama, both of Hino, Japan

[73] Assignee: Konica Corporation, Tokyo, Japan

[21] Appl. No.: 596,742

[22] Filed: Oct. 12, 1990

Related U.S. Application Data

[63] Continuation of Ser. No. 492,300, Feb. 28, 1990, abandoned, which is a continuation of Ser. No. 235,279, Aug. 22, 1988, abandoned.

[30] Foreign Application Priority Data

Aug. 24, 1987 [JP] Japan ................... 62-211067

[51] Int. Cl.$^5$ .............................................. G03C 7/38
[52] U.S. Cl. ...................................... 430/558; 430/384; 430/385
[58] Field of Search ............... 430/384, 385, 558 R

[56] References Cited

U.S. PATENT DOCUMENTS 2,296,271 9/1942 Dawson .............................. 430/558
4,818,672 4/1989 Masukawa et al. .................. 430/558

FOREIGN PATENT DOCUMENTS 0080905 6/1983 European Pat. Off. .
0249453 12/1987 European Pat. Off. .

*Primary Examiner*—Richard L. Schilling
*Attorney, Agent, or Firm*—Jordan B. Bierman

[57] ABSTRACT

A silver halide photographic light sensitive material is disclosed, which is contains a novel cyan coupler excellent in spectral absorption, absorption coefficient and fastness. The cyan coupler is represented by the following Formula I;

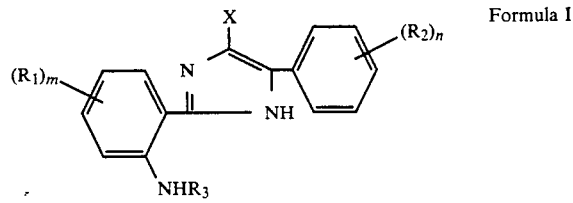

Formula I wherein $R_1$ and $R_2$ each represent a substituent; $R_3$ represents a hydrogen atom, an alkyl group, an aryl group, a —$COR_4$ group, a —$COOR_4$ group, a

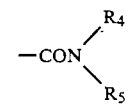

group, an —$SO_2R_4$ or an

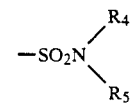

group in which $R_4$ represents an alkyl group, an aryl group or a heterocyclic group, $R_5$ represents a hydrogen atom or an alkyl group; X represents a hydrogen atom or a group capable of being split off upon reaction with the oxidized product of a color developing agent; m represent an integer of from 0 to 4; and n represents an integer of from 0 to 5.

7 Claims, 1 Drawing Sheet

PHOTOGRAPHIC MATERIAL WITH IMIDAZOLE CYAN COUPLER

This application is a continuation of application Ser. No. 07/492,300, filed Feb. 28, 1990, now abandoned, which is a continuation of application Ser. No. 235,279, filed Aug. 22, 1988, now abandoned.

FIELD OF THE INVENTION

The present invention relates to a silver halide color photographic light-sensitive material that contains a novel cyan coupler.

BACKGROUND OF THE INVENTION

Usually, a silver halide color photographic light-sensitive material contains a light-sensitive silver halide emulsion, as well as a so-called dye forming coupler that is capable of forming a dye upon reaction with an oxidation product of a color developing agent.

As cyan couplers, phenols and naphthols have been in wide use, some of these products being described, for example, in U.S. Pat. Nos. 2,309,929, 2,423,730, 2,474,293, 2,772,162 and 2,895,826, and Japanese Patent Publication Open to Public Inspection (hereinafter referred to as Japanese Patent O.P.I. Publication) No. 65134/1981.

The cyan dye images formed from such phenols or naphthols, however, incurs a serious problem in color reproduction. An absorption spectrum of a cyan dye formed thereby shows a disorderly boundary on the shorter wavelength side and has an undesirable irregular absorption in the green portion and in part in the blue portion. As a solution to this problem, it has been a usual practice, in negative films, to compensate the irregular absorption by masking using colored couplers. This practice, however, incurs the defect of retrogression in sensitivity. With respect to sensitive materials in reversal system, as well as with a color paper, color reproducibility remains impaired because of lack in effective means for the compensation.

SUMMARY OF THE INVENTION

The object of the present invention is to provide a silver halide color photographic light-sensitive material that contains a novel cyan coupler designed to form a cyan dye having a satisfactory spectral absorption characteristic featuring a sharp boundary on the shorter wavelength side and minimization of the irregular absorption in the green and blue portions and furthermore having a large value of absorption coefficient while good fastness is ensured with respect to the colored images obtainable.

The above-mentioned object can be accomplished by a silver halide color photographic light sensitive material comprising a support provided thereon at least one silver halide emulsion layer, wherein at least one of the silver halide emulsion layers contain a cyan coupler represented by the following formula I.

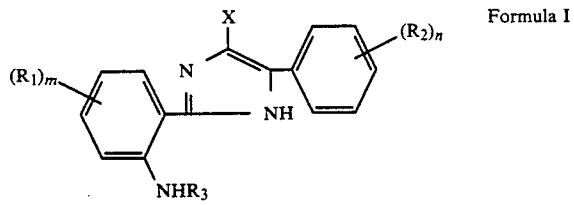

Formula I

In the formula, $R_1$ and $R_2$ independently represent a substituent group; m, an integer from 0 to 4; n, an integer from 0 to 5; $R_3$ represents a hydrogen atom, an alkyl group, aryl group, $-COR_4$ group, $-COOR_4$ group,

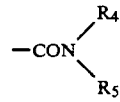

group, $SO_2R_4$ group or

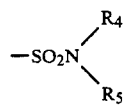

group;
$R_4$ represents an alkyl group, aryl group, heterocyclic group; $R_5$ represents a hydrogen atom or an alkyl group; X represents a hydrogen atom, or a group capable of being split off upon reaction with an oxidation product of a color developing agent.

DETAILED DESCRIPTION OF THE INVENTION

Figure 1:
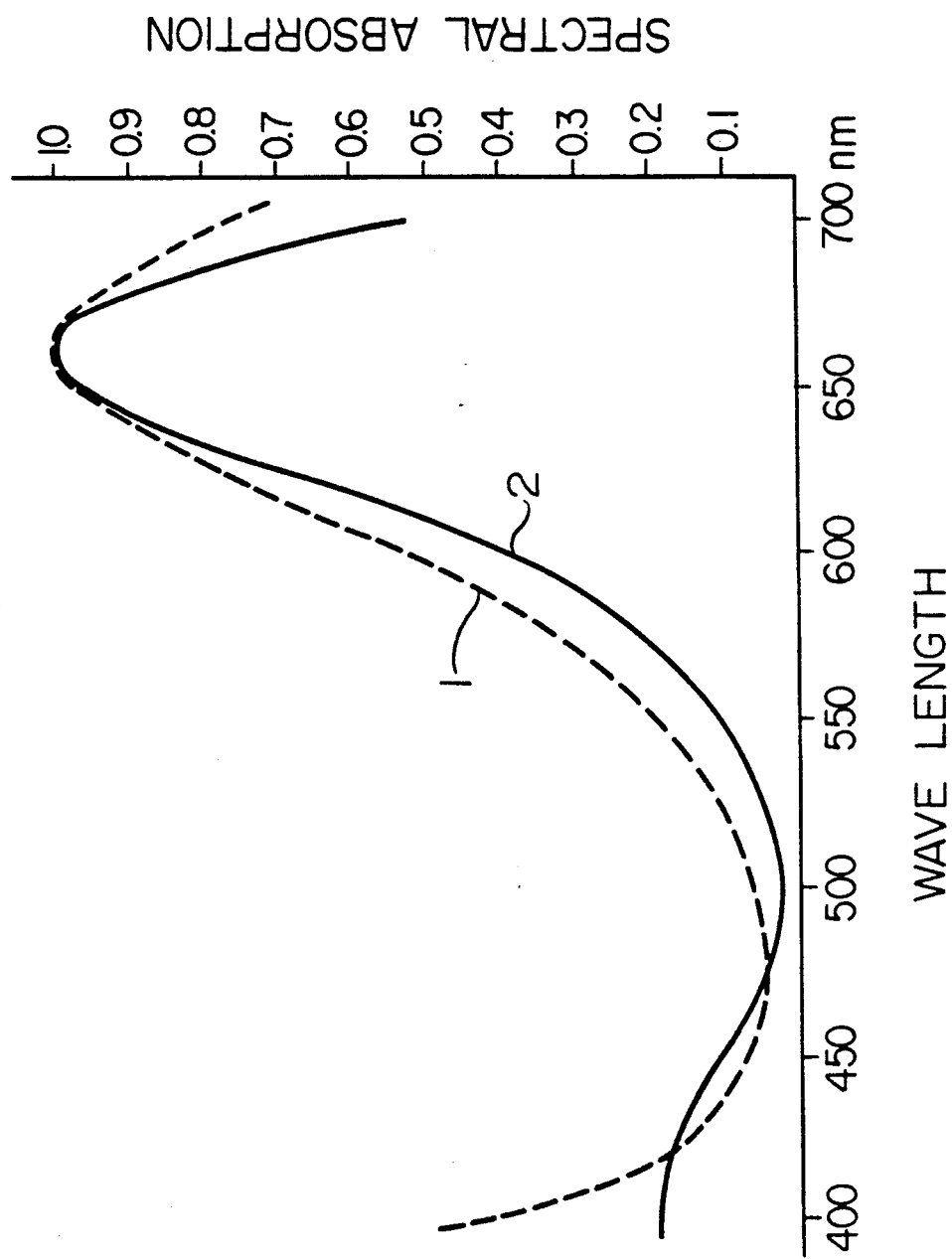
FIG. 1 includes spectral curves of developed Sample Nos. 1 and 2, up to the density level 1.0.

The use of the present invention in a preferred mode is to have one of $R_2$ in formula I occupied by a group represented as $-NHR_6$ and on the o-position on the imidazole ring such as in the following formula II.

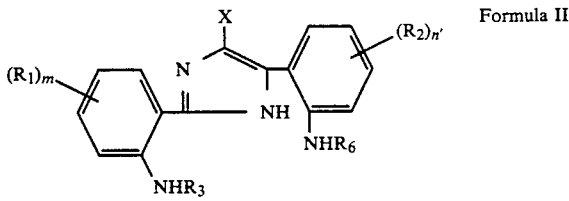

Formula II

In this formula, $R_1$, $R_2$ and $R_3$ have the meanings same as in formula I; and $R_6$ has the meaning same as $R_3$ in formula I, provided that n' is an integer from 0 to 4. The presence of the $-NHR_6$ group improves not only the absorptivity of the dye formed but also its heat resistance.

The above-mentioned formulas I and II are hereunder described in further detail. There is no specific restriction to the substituent groups represented by $R_1$ and $R_2$ in formulas I and II. Some examples useful therefor include halogen atoms, and groups of cyano, nitro, carboxy, alkyl, alkoxy, carbamoyl, sulfamoyl, acyl, acyloxy, alkoxycarbonyl, $-NHCOR_7$,

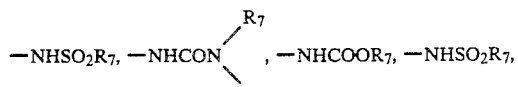

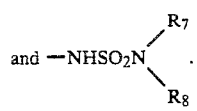

Preferable as an alkyl group represented by $R_1$ or $R_2$ is one of the straight chain or branched type with 1 to 22 carbon atoms, examples being methyl, ethyl, butyl, and dodecyl groups. The alkyl groups useful therefor include cycloalkyls, such as cyclohexyl, and also substituted alkyls, preferable substituent groups in the latter case being, for example, hydroxy, carboxy, cyano, and sulfo; or alkoxy with 1 to 22 carbon atoms.

Preferable as an alkoxy group therefor is one of the straight chain or branched type with 1 to 22 carbon atoms, examples being the groups of methoxy, ethoxy, i-propyloxy, octyloxy and dodecyloxy.

Examples of carbamoyl groups therefor are unsubstituted alkylcarbamoyl groups, such as ethylcarbamoyl and dodecylcarbamoyl, and substituted alkylcarbamoyl groups, such as diethylcarbamoyl, butyloxypropylcarbamoyl and dodecyloxy-propylcarbamoyl.

Examples of sulfamoyl groups are unsubstituted alkylsulfamoyl groups, such as ethylsulfamoyl, diethylsulfamoyl and dodecylsulfamoyl, and substituted alkylsulfamoyl groups, such as dodecylocypropylsulfamoyl.

Examples of arylcarbamoyl groups are phenylcarbamoyl group and substituted phenylcarbamoyl group, and examples of arylsulfamoyl groups are phenylsulfamoyl and various substituted phenylsulfamoyl groups.

Examples of acyl groups are acetyl, benzoyl, butanesulfonyl and benzenesulfonyl; examples of acyloxy groups are acetoxy, lauroyloxy and butanesulfonyloxy; and examples of alkoxycarbonyl groups are ethoxycarbonyl, i-propylocycarbonyl and 2-ethylhexyloxycarbonyl. —$NHCOR_7$ through

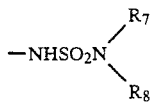

representing groups for $R_1$ and $R_2$ have the same meanings as —$NHCOR_4$ through

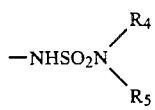

for —$NHR_3$ which are explained later.

Preferable as an alkyl group for $R_3$ is one of the straight chain or branched type with 1 to 32 carbon atoms, including a cycloalkyl group such as cyclohexyl group.

A substituted variant of such as alkyl group is also useful therefor, some typical preferable substituent groups being groups of hydroxy, carboxy, cyano, and sulfo; and alkoxy with 1 to 22 carbon atoms.

Preferable as an aryl group for $R_3$ is phenyl group or a substituted phenyl group having a group of nitro, amido, sulfonamido, or the like as a substituent group.

An explanation is given next with respect to $NHR_3$ where it represents a group of —$NHCOR_4$, —$NHCOOR_4$,

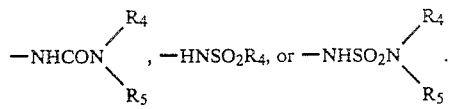

—$NHCOR_4$ represents an alkylamido group having 1 to 22 carbon atoms. Typical examples of an unsubstituted alkylamido group therefor are group of acetamido, butanamido, laurylamido and stearylamido. The useful groups include alicyclic amides such as cyclohexanecarbonamido group, groups with a branched structure such as 2-ethylhexanamido, and ones having an unsaturated linkage.

Examples of a substituted alkylamido group therefor are halogen-substituted alkylamido groups, such as groups of monochloroacetamido, triohloroacetamido and perfluorobutanamido, and phenoxy-substituted alkylamidos, such as groups of m-pentadecylphenoxyacetamido, α-(2,4-di-t-amylphenoxy)pentanamido, α-(2,4-di-t-acylphenoxy) acetamido, and o-chlorophenoxymyristic acid amido.

—$NHCOR_4$ may also represent an arylamido group whose typical examples are benzamido and naphthoamido both as an unsubstituted arylamido, and such substituted arylamidos as p-t-butylbenzamido and p-methylbenzamido both as an alkyl-substituted benzamido, p-methoxybenzamido and o-dodecyloxy-benzamido both as an alkoxy-substituted benzamido, p-acetamidobenzamido, m-lauroylamidobenzamido and m-(2,4-di-t-amyl-phenoxyacetamido)benzamido all as an amido-substituted benzamido, and o-hexadecanesulfonamidobenzamido and p-butane-sulfonamidobenzamido both as a sulfonamido-substituted benzamido.

—$NHCOOR_4$ represents an alkoxycarbonylamino group, either in the substituted state or unsubstituted, with 1 to 22 carbon atoms, typical examples being, for example, ethoxycambonylamino, i-propoxycarbonylamino, octyloxycarbonylamino, decyloxycarbonyl, and methoxyethoxycarbonylamino. —$NHCOOR_4$ may also represent an aryloxycarbonyl group typified by phenoxycarbonyl.

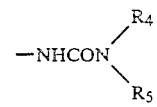

represents a dialkylcarbamoylamino, typical examples being dimethylcarbamoylamido and diethylcarbamoylamino.

—$NHSO_2R_4$ represents an alkylsulfonamido group or an arylsulfonamido group

Examples of the alkylsulfonamido group are methanesulfonamido, butanesulfonamido and dodecanesulfonamido, each being an unsubstituted alkylsulfonamido with 1 to 22 carbon atoms, and benzylsulfonamido as a substituted alkylsulfonamido.

Examples of the arylsulfonamido group are benzenesulfonamido and naphthalenesulfonamido both as an unsubstituted arylsulfonamido and such substituted arylsulfonamido as p-toluenesulfonamide, 2,4,6trimethyl-benzensulfonamido and p-dodecylbenzensulfonamido all as an alkyl-substituted benzensulfonamido and p-dodecyloxybenzensulfonamido and butyloxybenzensulfonamido both as an alkoxy-substituted benzensulfonamido.

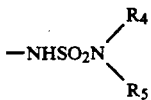

represents a sulfamoylamino group, preferable examples of which are dimethylsulfamoylamino and dibutylsulfamoylamino both as a dialkylsulfamoylamino.

It is preferable for the above-mentioned groups to assume an arrangement where —$NHR_3$ can be represented as —$NHCOR_4$, —$NHCOOR_4$ or —$NHSO_2R_4$, and especially so where —$NHR_6$ can be represented as —$NHCOR_7$, —$NHCOOR_7$ or —$NHSO_2R_7$, that is, where one of these groups is substituted at the o-position on each phenyl group at the 2- and 4-positions on the imidazole ring.

Those applicable as a group represented by X, which is capable of being split off upon reaction with an oxidation product of a color developing agent, are groups known to the photographic material industry as active point substituent groups, but halogen atoms such as chlorine and bromine are preferable for the purpose.

There are shown hereunder examples typifying the cyan couplers of the diphenylimidazole type (hereinafter referred to as "the cyan coupler of the invention"), represented by general formula I, on the understanding that the scope and spirit of the present invention are not restricted to these examples.

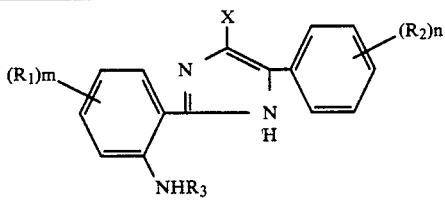

| Compound | X | $R_1$ | $R_2$ | $R_3$ | m | n |
|---|---|---|---|---|---|---|
| 1 | H | H | H | —COCHO—[phenyl with $C_5H_{11}(t)$, $C_5H_{11}(t)$]—, with $C_3H_7(i)$ branch | 0 | 0 |
| 2 | Cl | H | H | —COCHO—[phenyl with $C_5H_{11}(t)$, $C_5H_{11}(t)$]—, with $C_3H_7(i)$ branch | 0 | 0 |
| 3 | Cl | H | 4-$NHCOOC_2H_5$ | —COCHO—[phenyl with $C_5H_{11}(t)$, $C_5H_{11}(t)$]—, with $nC_4H_9$ branch | 0 | 1 |
| 4 | H | H | 4-NHCOCHO—[phenyl with $C_5H_{11}(t)$, $C_5H_{11}(t)$]—, with $C_2H_5$ branch | —$COOC_4H_9(i)$ | 0 | 1 |
| 5 | H | H | 4-$NHCOC_2H_5$ | —$SO_2$—[phenyl]—$OC_{12}H_{25}$ | 0 | 1 |
| 6 | H | H | 3-NHCO—[phenyl] | —$SO_2$—[phenyl with $OC_8H_{17}$, $C_8H_{17}(t)$] | 0 | 1 |

-continued
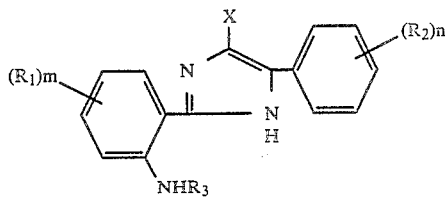
| Compound | X | $R_1$ | $R_2$ | $R_3$ | m | n |
|---|---|---|---|---|---|---|
| 7 | H | H | 2-Cl, 4-Cl | —COCHO(C₄H₉)— attached to 2,4-di-$C_5H_{11}(t)$-phenoxy | 0 | 2 |
| 8 | Cl | H | 4-$OC_{16}H_{33}$ | —$COOC_2H_6$ | 0 | 1 |
| 9 | Cl | H | 4-$SO_2NH(CH_2)_3OC_{12}H_{25}$ | —CO—phenyl | 0 | 1 |
| 10 | H | H | 3-$NHCOCH_2O$—[2,4-di-$C_5H_{11}(t)$-phenyl] | —$SO_2N(CH_3)_2$ | 0 | 1 |
| 11 | H | H | 4-$NHCOCH_2O$—[2,4-di-$C_5H_{11}(t)$-phenyl] | H | 0 | 1 |
| 12 | H | H | 4-$NHCOCH_2O$—[2,4-di-$C_5H_{11}(t)$-phenyl] | 4-$NO_2$-phenyl | 0 | 1 |
| 13 | H | H | H | —$SO_2$—[2-$OC_4H_9$-5-$C_8H_{17}(t)$-phenyl] | 0 | 0 |
| 14 | Cl | H | H | —$SO_2C_6H_{17}$ | 0 | 0 |
| 15 | Cl | H | 2-Cl, 4-Cl | —$SO_2$—[2-$OC_8H_{17}$-5-$C_8H_{17}(t)$-phenyl] | 0 | 2 |

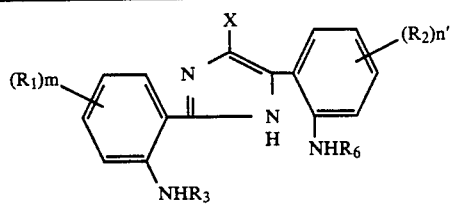

| Compound | X | R₁ | R₂ | R₃ | R₆ | m | n' |
|---|---|---|---|---|---|---|---|
| 16 | Cl | H | H | —COCH₃ | —COCHO—C₆H₃(C₅H₁₁(t))₂, with C₄H₉ branch | 0 | 0 |
| 17 | H | H | H | —CO—C₆H₅ | —COCHO—C₆H₃(C₅H₁₁(t))₂, with C₄H₉ branch | 0 | 0 |
| 18 | H | H | H | —COOC₄H₉(i) | —COCHO—C₆H₃(C₅H₁₁(t))₂, with C₄H₉ branch | 0 | 0 |
| 19 | Cl | H | H | —SO₂—C₆H₃(OC₈H₁₇)(C₈H₁₇(t)) | —COCHO—C₆H₃(C₅H₁₁(t))₂, with C₄H₉ branch | 0 | 0 |
| 20 | Cl | H | H | —CO—C₆H₅ | —COCHO—C₆H₃(C₅H₁₁(t))₂, with C₄H₉ branch | 0 | 0 |
| 21 | Cl | H | H | —COC₄H₉(i) | —COCHO—C₆H₃(C₅H₁₁(t))₂, with C₄H₉ branch | 0 | 0 |
| 22 | H | H | H | —COCH₃ | —SO₂—C₆H₃(OC₈H₁₇)(C₈H₁₇) | 0 | 0 |
| 23 | H | H | H | —CO—C₆F₄ (tetrafluorophenyl) | —COCHO—C₆H₃(C₅H₁₁(t))₂, with C₃H₇(i) branch | 0 | 0 |

-continued

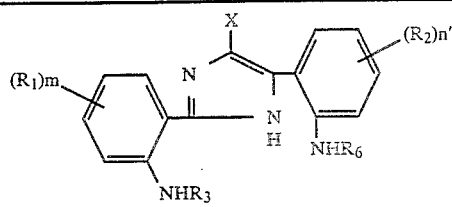

| Compound | X | R₁ | R₂ | R₃ | R₆ | m | n' |
|---|---|---|---|---|---|---|---|
| 24 | H | H | H | —CON(CH₃)₂ | —COCHO—⟨C₅H₁₁(t), C₅H₁₁(t)⟩ with C₃H₇(i) | 0 | 0 |
| 25 | H | H | H | —CONH—⟨Cl, CN⟩ | —COCHO—⟨C₅H₁₁(t), C₅H₁₁(t)⟩ with C₃H₇(i) | 0 | 0 |
| 26 | H | H | H | —SO₂CH₃ | —COCHO—⟨Cl⟩ with C₁₂H₂₅ | 0 | 0 |
| 27 | H | H | H | —SO₂N(C₂H₅)₂ | —COCHO—⟨C₅H₁₁(t), C₅H₁₁(t)⟩ with C₆H₁₃ | 0 | 0 |
| 28 | H | H | H | —SO₂—⟨OC₁₂H₂₅⟩ | —COCH₃ | 0 | 0 |
| 29 | H | H | H | —COOC₄H₉(i) | —COCHO—⟨C₄H₉(t), OH⟩ with C₁₂H₂₅ | 0 | 0 |
| 30 | H | H | H | —COOC₂H₅ | —COC₁₁H₂₃ | 0 | 0 |
| 31 | Cl | H | H | —CO—⟨NHCOC₁₁H₂₃⟩ | —COC₃H₇(i) | 0 | 0 |
| 32 | Cl | H | H | —COC₂F₅ | —COCHO—⟨C₅H₁₁(t), C₅H₁₁(t)⟩ with C₃H₇(i) | 0 | 0 |
| 33 | H | H | H | —⟨NO₂⟩ | —COCHO—⟨C₅H₁₁(t), C₅H₁₁(t)⟩ with C₄H₉ | 0 | 0 |

-continued

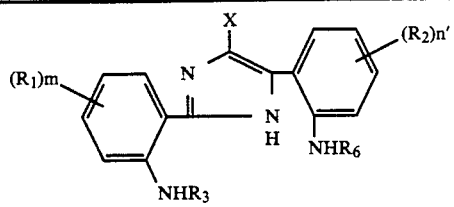

| Compound | X | $R_1$ | $R_2$ | $R_3$ | $R_6$ | m | n' |
|---|---|---|---|---|---|---|---|
| 34 | H | H | H | —C₆H₄—NHCOCH₃ (p) | —COCH(C₄H₉)O—C₆H₃[C₅H₁₁(t)]₂ | 0 | 0 |
| 35 | H | H | H | —C₂H₅ | —COCH(C₄H₉)O—C₆H₃[C₅H₁₁(t)]₂ | 0 | 0 |
| 36 | H | H | H | —COOC₄H₉(i) | —SO₂—C₆H₃(OC₈H₁₇)(C₈H₁₇) | 0 | 0 |
| 37 | Cl | H | 4-Cl | —COOC₄H₉(i) | —COCH(C₃H₇(i))O—C₆H₃[C₅H₁₁(t)]₂ | 0 | 1 |
| 38 | Cl | H | 5-OCH₃ | —COOC₄H₉(i) | —COCH(C₃H₇(i))O—C₆H₃[C₅H₁₁(t)]₂ | 0 | 1 |
| 39 | Cl | H | 4,5-(CH₃)₂ | —COCH₃ | —COCH(C₃H₇(i))O—C₆H₃[C₅H₁₁(t)]₂ | 0 | 2 |
| 40 | Cl | H | 5-Br | —COCH₃ | —COCH(C₃H₇(i))O—C₆H₃[C₅H₁₁(t)]₂ | 0 | 1 |
| 41 | H | H | H | —SO₂CH₃ | —COOCH₂CH(C₂H₅)C₄H₉ | 0 | 0 |
| 42 | Cl | H | H | —SO₂CH₃ | —SO₂—C₆H₃(OC₈H₁₇)(C₅H₁₁(t)) | 0 | 0 |

-continued
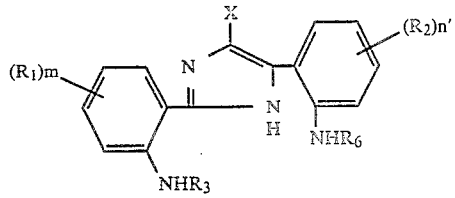
| Compound | X | R₁ | R₂ | R₃ | R₆ | m | n' |
|---|---|---|---|---|---|---|---|
| 43 | Cl | H | H | —SO₂—C₆H₃(OC₄H₉)(C₈H₁₇(t)) | —COCH₃ | 0 | 0 |
| 44 | H | H | H | —SO₂N(CH₃)₂ | —SO₂—C₆H₂(OC₄H₉)(C₅H₁₁(t))(C₅H₁₁(t)) | 0 | 0 |
| 45 | H | H | H | —SO₂C₈H₁₇ | —SO₂C₈H₁₇ | 0 | 0 |
| 46 | H | H | H | —SO₂—C₆H₃(OC₄H₉)(C₈H₁₇(t)) | —SO₂—C₆H₄—OC₄H₉ | 0 | 0 |
| 47 | Cl | H | H | —COOC₄H₉(i) | —COOCH₂CH(C₂H₅)C₄H₉ | 0 | 0 |
| 48 | H | H | H | —CON(CH₃)₂ | —COCH(C₃H₇(i))O—C₆H₃(C₅H₁₁(t))(C₅H₁₁(t)) | 0 | 0 |
| 49 | Cl | H | H | —SO₂CH₃ | —COCH(C₁₂H₂₅)O—C₆H₄Cl | 0 | 0 |
| 50 | Cl | H | H | —SO₂—C₆H₄—OC₁₂H₂₅ | —COC₂H₅ | 0 | 0 |
| 51 | Cl | H | H | —COOC₄H₉(i) | —SO₂—C₆H₃(OC₄H₉)(C₈H₁₇(t)) | 0 | 0 |

-continued
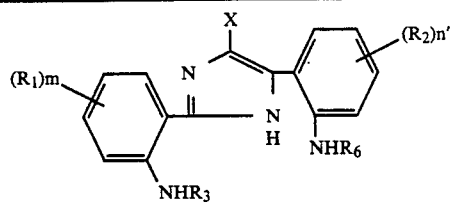
| Compound | X | R1 | R2 | R3 | R6 | m | n' |
|---|---|---|---|---|---|---|---|
| 52 | H | H | H | —SO2—(2-OC8H17, 4-C8H17(t))phenyl | —COCH(C4H9)O—(2-C5H11(t), 4-C5H11(t))phenyl | 0 | 0 |
| 53 | H | H | H | —SO2N(CH3)2 | —SO2—(2-OC4H9, 3-C5H11(t), 5-C5H11(t))phenyl | 0 | 0 |
| 54 | Cl | H | H | —SO2—(2-OC4H9, 3-C5H11(t), 5-C5H11(t))phenyl | —SO2CH3 | 0 | 0 |
| 55 | Cl | H | H | —SO2C8H17 | —SO2N(C2H5)2 | 0 | 0 |
| 56 | H | H | H | —SO2—(2-OC4H9, 4-C8H17(t))phenyl | —SO2N(CH3)2 | 0 | 0 |
| 57 | Cl | H | H | —SO2N(C2H5)2 | —SO2N(C2H5)2 | 0 | 0 |
| 58 | Cl | H | H | —SO2—(2-OC8H17, 4-C8H17(t))phenyl | —SO2—(2-OC8H17, 4-C8H17(t))phenyl | 0 | 0 |
| 59 | Cl | H | H | —SO2—(2-OC8H17, 4-C8H17(t))phenyl | —COOCH2CH(C2H5)C4H9 | 0 | 0 |
| 60 | Cl | H | H | —SO2-(3-pyridyl) | —CO(CH)2OCOCH2O—(2-C8H17, 4-Cl)phenyl | 0 | 0 |

-continued

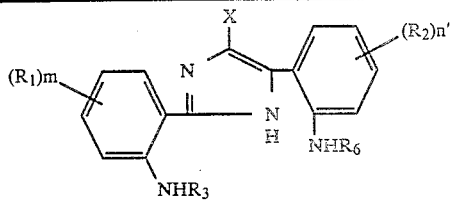

| Compound | X | R₁ | R₂ | R₃ | R₆ | m | n' |
|---|---|---|---|---|---|---|---|
| 61 | Cl | H | H | −SO₂−⟨benzene-3,4-diOH⟩ | −CO(CH₂)₃O−⟨benzene with N(C₄H₉)₂ and C₈H₁₇(t)⟩ | 0 | 0 |
| 62 | Cl | H | H | −SO₂(CH₂)₃O−⟨hydantoin with N−C₁₂H₂₅⟩ | −CO−⟨benzene-3,4,5-triOH⟩ | 0 | 0 |
| 63 | Cl | H | H | −COCHO−⟨C₅H₁₁⟩−⟨C₆H₄−NHSO₂C₄H₉⟩ | −COCHO−⟨C₅H₁₁⟩−⟨o-CN-phenyl⟩ | 0 | 0 |
| 64 | Cl | H | H | −COCHO−⟨C₁₂H₂₅⟩−⟨benzene with C₄H₉(t) and OH⟩ | −COCHO−⟨C₅H₁₁⟩−⟨benzene with CN and C₅H₁₁(t)⟩ | 0 | 0 |
| 65 | Cl | H | H | −SOCHNHSO₂CH₃ / CH₃ | −COCHO−⟨C₁₂H₂₅⟩−⟨C₆H₄−N(isothiazolidine-S,S-dioxide)⟩ | 0 | 0 |
| 66 | Cl | H | H | −COCHO−⟨C₂H₅⟩−⟨benzene with C₄H₉(t) and methylenedioxy⟩ | −COCHO−⟨C₁₀H₂₁⟩−⟨benzene with Cl, SO₂−⟨C₆H₃(Cl)(OH)⟩⟩ | 0 | 0 |

The typical methods for synthesizing the couplers of the invention are as follows.

Synthesis 1 (Synthesis of compound 1)

Synthesis of 2-(o-nitrophenyl)-4-phenylimidazole 11.8 g of o-nitrobenzamidine, 7.11 g of phenacyl bromide, and 80 ml of chloroform were stirred together at a room temperature for one hour. While crystals began to precipitate, the mixture was refluxed under boil on a hot water bath for two more hours. After cooling, o-nitrobenzamidine hydrobromide which had precipitated was filtered off, and then the filtrate was concentrated, dissolved in acetonitrile, and with addition of a small quantity of concentrated hydrochloric acid made into a hydrochloride. Through filtering, washing with acetonitrile, and drying this product, 7.5 g of hydrochloride was obtained therefrom. The product was freed with ethyl acetate-aqueous ammonia to from 6.1 g of oily matter.

Synthesis of Compound 1

6.1 g of the 2-(o-nitrophenyl)-4-phenylimidazole was dissolved in 100 ml of alcohol and made to undergo catalytic reduction by hydrogen at atmospheric pressure with addition of 0.3 g of Pd-C catalyst (for about two hours).

The catalyst was filtered out and the filtrate was concentrated. The amino substance remaining as a pale brown powder was used unchanged, without special refining, in the following reaction. This amino substance was dissolved in 80 ml of acetonitrile and stirred at a room temperature for four hours with addition of 2.3 g of pyridine and 10.5 g of α-(2,4-di-t-amylphenoxy)-α-i-propylacetyl chloride.

The crystals which had precipitated were filtered off to produce 6.4 g of hydrochloride. By freeing this product in ethyl acetate-aqueous ammonia, 5.8 g of 2-[2-{α(2,4-di-t-amylphenoxy)-α-i-propyl}acetamido]phenyl-4-phenylimidazole was obtained.

Synthesis 2 (Synthesis of Compound 17)

Synthesis of 2-(2-nitrophenyl)-4-[2-{(2,4-di-t-amylphenoxy) hexanamido}phenyl]imidazole 8.92 g of 2-[2-(2,4-di-t-amylphenoxy)hexanamido]-α-bromoacetophenone, and 5.4 g of o-nitrobenzoamidine were stirred together in 100 ml of chloroform at a room temperature. Crystals began to precipitate. The mixture was them refluxed under boil on a hot water bath for two hours. After cooling, the crystals were filtered off and the filtrate was concentrated. Thus produced yellowish brown oily residue was again dissolved in 50 ml of acetonitrile and, after addition of 2 cc of concentrated hydrochloric acid, allowed to stand overnight. The crystals which had precipitated were filtered off to produce 7.60 g of hydrochloride after drying.

This product was suspended in a mixture of 100 ml of ethyl acetate and 100 ml of water with addition of 5 ml of aqueous ammonia. The crystals were dissolved so that a layer of ethyl acetate was made to contain the product in solution. This layer of ethyl acetate was washed with water by a conventional method and, after dehydration, the concentrated thick syrup-like residue solidified with time to form 7.36 g of 2-(2-nitrophenyl)-4-[2-{2-(2,4-di-t-amylphenoxy)hexanamido}phenyl-]imidazole in the amorphous solid state.

Synthesis of 2-(2-aminophenyl)-4-[2-{2-(2,4-di-t-amyl phenoxy)hexanamido}phenyl]imidazole 6.8 g of the previously mentioned nitro substance was dissolved in 50 ml of ethanol and made to undergo catalytic reduction by hydrogen at atmospheric pressure with addition of 0.34 g of Pd-C catalyst. The reaction ended in about two hours. After removing the catalyst, the filtrate was concentrated to produce the amino substance, which was used unchanged, without special refining, in the following reaction.

Synthesis of Compound 17

One gram of the previously mentioned amino substance was dissolved in 15 ml of acetonitrile and 0.3 g of pyridine was added thereto. To this mixture was added 0.26 g of benzoyl chloride and the mixture was allowed to undergo a reaction at a room temperature for two hours. The acetonitrile was removed by distillation under reduced pressure and then oily residue was dissolved in ethyl acetate.

After washing with aqueous ammonia, a layer of ethyl acetate which had been formed was dehydrated with magnesium sulfate and allowed to concentrate to dryness. The thick syrup-like reside was re-dissolved in 10 ml of acetonitrile and allowed to stand with addition of several droplets of concentrated hydrochloric acid. The coupler to be produced precipitated gradually in the form of hydrochloride, which was filtered off, washed and dried to form 0.74 g of hydrochloride.

This hydrochloride was again freed, as in the preceding example, with ethyl acetate-diluted aqueous ammonia. The oily substance was re-dissolved in several ml of acetonitrile and allowed to stand and the precipitate was filtered off and dried finally to form 0.61 g of the desired product. (boiling point: 167°-170° C.)

Synthesis 3 (Synthesis of Compound 18)

0.84 g of the amino substance in the foregoing synthesis 2 was dissolved in a mixture of 10 ml of acetonitrile and 0.3 g of pyridine and, after adding 0.22 g (molar ratio, 1.1) of isobutyl chloroformic acid ester at a room temperature, the mixture was stirred for two hours. The solid which had precipitated was filtered off, and 0.79 g of it (hydrochloride) was suspended in ethyl acetate and, after adding 5% aqueous sodium bicarbonate solution and a small quantity of pyridine, dissolved completely by thorough stirring. After washing with water and drying with magnesium sulfate, the product was formed into a white amorphous solid by concentration. This solid could not be recrystallized but was found to be pure by thin layer chromatography and was also identified as desired 2-(2-i-butoxycarbonylamino)phenyl-4-[2-{2-(2,4-di-t-amylphenoxy)hexanamido}phenyl-]imidazole by mass spectra and NMR.

Synthesis 4 (Synthesis of Compound 20)

0.6 g of the compound 14, which was obtained in the foregoing synthesis 2, was dissolved in 10 ml of chloroform and, after adding 0.13 g of N-chlorosuccinimide, made to react at a room temperature for two hours. After concentrating it, the residue of the product was dissolved in ethyl acetate and then the layer of ethyl acetate was washed with water. After dehydration with anhydrous sodium sulfate, the ethyl acetate layer was concentrated and the residue was dissolved in acetonitrile and allowed to stand overnight. The crystals which had precipitated was filtered off, washed with acetonitrile and dried finally to form 0.4 g of Compound 17. (melting point: 177°-180° C.)

Synthesis 5 (Synthesis of Compound 19)

Synthesis of 2-[2-(2-octyloxy-5-t-octylbenzensulfonamido)-phenyl]-4-[2-{α-(2,4-di-t-amylphenoxy)hexanamido} phenyl]imidazole One gram (1.72 millimol) of 2-(2-aminophenyl)-4-[2-{α-(2,4-di-t-aminophenoxy)hexanamido}phenyl-]imidazole was dissolved in 10 ml of acetonitrile and 0.3 g of pyridine was added thereto. 0.79 g (1.89 millimol) of 2-octyloxy-5-t-octylbenzensulfonylchloride was added at a room temperature with stirring, and the solution was stirred continuously for two hours. The reactant was extracted from the solution with ethyl acetate and 5% aqueous sodium hydrogen carbonate solution, and the ethyl acetate layer was washed with water and dried with magnesium sulfate. The solvent was removed therefrom by distillation and the residue was dissolved in acetone, acidified by adding several droplets of concentrated hydrochloric acid and allowed to stand overnight. The crystals which had precipitated were filtered off (1.45 g, 84.6% yield), suspended in ethyl acetate, and dissolved completely by addition of aqueous ammonia. The ethyl acetate layer was washed with water, dried with magnesium sulfate, and after removing the solvent therefrom by distillation, dried under reduced pressure to from 1.2 g of an amorphous solid. The product was identified as Compound 19 by thin layer chromatography, mass spectra and NMR.

Synthesis of Compound 19

By reacting the above-mentioned compound with N-chlorosuccinimide in the same manner as in Synthesis 4, Compound 19 was obtained as an amorphous solid.

The cyan couplers of the invention are used in med-sensitive silver halide emulsion layers, mainly at a rate of $2 \times 10^{-3}$ to $8 \times 10^{-1}$ mol per mol silver halide, preferably at a rate of $1 \times 10^{-2}$ to $5 \times 10^{-1}$ mol per mol silver halide.

There are various ways in which the cyan couplers of the invention are incorporated into silver halide emulsion layers. For example, the cyan coupler of the invention is first dissolved in a high boiling organic solvent with a boiling point of over 150° C. and/or in a low boiling organic solvent with a boiling point of 30° to 150° C., and then dispersed in a hydrophilic colloid, examples of the first-mentioned high boiling organic solvent being alkyl phthalates (dibutylphthalate, diontylphthalate, and the like) and phosphates (diphenylphosphate, triphenylphosphate, tricresylphosphate, dioctylbutylphosphate, and the like), and examples of the latter-mentioaed low boiling organic solvent being ethyl acetate, butyl acetate, ethyl propionate, secondary butyl alcohol, methyl isobutyl ketone, and methyl cellosolve acetate. Ordinarily, it is preferable to use both a high boiling organic solvent and a low boiling organic solvent, both exemplified above, in a mixture.

There is no specific restriction to the silver halide grains which are to be used in silver halide emulsion layers in a photographic light-sensitive material embodying the present invention, but where the light-sensitive material is required to have rapid processability, such as in the case of color printing paper, it is preferable for the silver halide grains to be of silver chloride, or silver chloride-containing silver chloro-bromide or silver chlor-iodide.

The especially preferable, in meeting such a requirement, is the use of silver halide grains for rapid processing which have a silver chloride content of not less than 90 mol %.

In such silver halide grains of the rapid processing type having a silver chloride content of not less than 90 mol %, it is desirable for the silver bromide content to be not more than 5 mol %, and for the silver iodide content to be not more than 0.5 mol %, more desirable for the silver halide grains to be of silver chloro-bromide having the silver bromide content to be 0.1 to 1.0 mol %.

Such silver halide grains specially adapted for rapid processing can be used independently or in mixture with another type of silver halide grains of a different composition. It is also practical to mix the silver halide grains of the rapid processing type with those with a silver chloride content of less than 10 mol %.

In a silver halide emulsion layer where the silver halide grains for rapid processing are contained, it is desirable for the silver halide grains for rapid processing to be used in a proportion of not less than 60 wt %, in particular, not less than 80 wt % per total content of the silver halide grains therein.

The silver halide emulsion used in this invention can be a polydispersed emulsion, i.e. an emulsion of a wider grain size distribution; however, the preferred emulsion is a monodispersed emulsion.

The emulsion containing such silver halide grains may be chemically sensitized with active gelatin, sulfur sensitizer, selenium sensitizer, reducing sensitizer, noble metal sensitizer, or the like.

The silver halide emulsion of the invention may be spectrally sensitized with a relevant sensitization dye to provide sensitivity to an intended spectral region.

The so-constituted silver halide photographic light-sensitive material of the invention can be, for example, a color negative film, color positive film, and a color print paper.

The silver halide color photographic light-sensitive materials of the invention, typified by a color paper, are multi-color silver halide photographic light-sensitive materials. To enable the subtractive color process, each of the materials usually comprises a support provided thereon layers laminated in an arbitrary number and order, wherein the layers comprise not only silver halide emulsion layers individually containing a photographic coupler, i.e. a magenta coupler, yellow coupler or cyan coupler, but also non-light-sensitive layers. The number and order of the layers are arbitrarily changed based on the important performance criteria and nature of usage of the light-sensitive material.

The particularly preferable order of layers in the silver halide color photographic light-sensitive material is as follows: on a support are formed, sequentially, a yellow dye-image forming layer, intermediate layer, magenta dye-image forming layer, intermediate layer, cyan dye-image forming layer, intermediate layer, and protective layer.

The silver halide color photographic light-sensitive material of this invention may arbitrarily contain an anti color foggant, image stabilizer, hardener, plasticizer, polymer latex, ultraviolet absorbent, formalin scavenger, mordant, development accelerator, development retardant, fluorescent whitening agent, matting agent, lubricant, antistatic agent, surface active agent, or the like.

When developing a silver halide color photographic light-sensitive material of the invention, various color developing processes are applicable.

Since containing the cyan coupler of the invention, the silver halide color photographic light-sensitive material excels in both color reproduction and dye-forming properties, and, in addition, a cyan image formed exhibits excellent fastness.

EXAMPLES

EXAMPLE 1

10 g comparative coupler CC-1 defined below, and 10 g dioctylphthalate were added to 20 ml ethyl acetate and heated to 50° C. and thoroughly dissolved therein, and then, the solution was blended with 100 ml aqueous solution containing 0.4 g Alkanol XC (sodium diisopropylnaphthalene sulfonate, manufactured by DuPont), thereby the mixture solution was stirred and subjected to ultrasonic homogenization. This coupler dispersion was added to 400 g photographic emulsion containing 35 g silver chloro-bromide (silver chloride content, 99%) and 40 g gelatin, to which 40 ml of 2% aqueous solution containing sodium 2,4-dichloro-6-hydroxy-s-triazine as a hardener was added, and the pH was adjusted to 6.0. Thus obtained the emulsion the coupler coating solutions was uniformly applied onto a subbed triacetyl cellulose film base. Thus Sample No. 1 was obtained.

Next, Sample Nos. 2 through 12 were prepared in a manner identical with that of Sample No. 1, except that coupler CC-1 was replaced with equivalent mol of cyan coupler of the invention 2, 3, 16, 20, 43, 21, 23, 15, 58, 59, or 44.

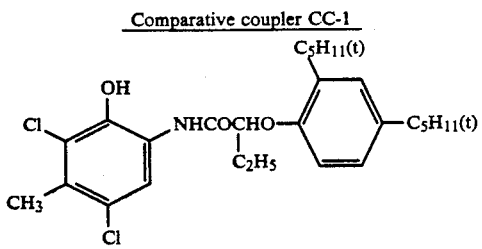

Comparative coupler CC-1

After being exposed through an optical wedge for sensitometry, these samples were subjected to color developing, bleach-fixing, and stablizing in accordance with the treatment procedure defined below, thereby the sensitivity and maximum density of each sample were determined.

FIG. 1 shows the spectral absorption curves measured at the point having 1.0 of density on colored Sample Nos. 1 and 2.

Each treated sample was allowed to stand for 21 days under the conditions of 60° C. and relative humidity of 50% and was examined for heat resistance. The results are listed in Table 1.

| Treatment Procedure | | |
| --- | --- | --- |
| Color developing | 35° C. | 45 sec. |
| Bleach-fixing | 35° C. | 45 sec. |
| Stabilizing | 35° C. | 1 min. 30 sec. |
| Drying | 60~80° C. | 2 min. |

The composition of each processing solution was as follows:

| Color-developer | |
| --- | --- |
| Water | 800 ml |
| Triethanolamine | 11 ml |
| N,N-diethylhydroxylamine (85% aqueous solution) | 6 ml |
| Potassium chloride | 2.3 g |
| Potassium sulfite | 0.3 g |
| Potassium carbonate | 30 g |
| Sodium tetrapolyphosphate | 2.0 g |
| N-ethyl-N-$\beta$-methanesulfonamidoethyl-3-ethyl-4-aminaniline sulfate | 5.2 g |

Water was added to prepare one liter solution, that was adjusted to pH=10.1 with 20% potassium hydroxide or 10% dilute sulfuric acid.

| Bleach-fixer | |
| --- | --- |
| Water | 800 ml |
| Ferric ammonium ethylenediaminetetraacetate | 65 g |
| Disodium ethylenediaminetetraacetic acid | 5 g |
| Ammonium thiosulfate | 60 g |
| Sodium hydrogen sulfite | 10 g |
| Sodium metabisulfite | 2 g |
| Sodium chloride | 10 g |

Water was added to prepare one liter solution, that was adjusted to pH=5.6 with dilute sulfuric acid.

| Stabilizer | |
| --- | --- |
| 5-chloro-2-methyl-4-isothiazoline-3-one | 1.0 g |
| 1-hydroxyethyledene-1,1-diphosphate | 2.0 g |

Water was added to prepare one liter solution, that was adjusted to pH=7.0 with sulfuric acid or potassium hydroxide.

TABLE 1

| Sample No. | Coupler | Sensitivity[1] | Dmax | Heat resistance[2] |
| --- | --- | --- | --- | --- |
| 1 (Comparative) | CC-1 | 100 | 1.83 | 0.72 |
| 2 (Invention) | Example compound 2 | 100 | 2.00 | 0.75 |
| 3 (Invention) | Example compound 3 | 101 | 2.05 | 0.76 |
| 4 (Invention) | Example compound 16 | 100 | 2.20 | 0.83 |
| 5 (Invention) | Example compound 20 | 103 | 2.08 | 0.85 |
| 6 (Invention) | Example compound 43 | 102 | 2.12 | 0.84 |
| 7 (Invention) | Example compound 21 | 101 | 2.18 | 0.86 |
| 8 (Invention) | Example compound 23 | 104 | 2.15 | 0.82 |
| 9 (Invention) | Example compound 15 | 105 | 2.25 | 0.90 |
| 10 (Invention) | Example compound 58 | 110 | 2.40 | 0.98 |
| 11 (Invention) | Example compound 59 | 110 | 2.45 | 0.97 |
| 12 (Invention) | Example compound 44 | 105 | 2.14 | 0.84 |

[1] Relative value based on the sensitivity of Sample No. 1, i.e. 100
[2] Post heat-resistance test density of an area whose initial density being 1.0

As can be understood from the results in Table 1, every sample incorporating a coupler of the invention as a cyan coupler exhibits not only higher maximum density, but excellent effects in terms of the heat resistance of a resultant dye image.

It is apparent from the spectral absorption curve, in FIG. 1, of a colored dye that is obtainable from the coupler of the invention, that a coupler of the invention forms a secondary-absorption-free dye that is capable of forming a sharp dye image.

EXAMPLE 2

On a paper support provided with polyethylene lamination on both faces thereof, the following layers were sequentially formed by coating, whereby multilayer silver halide color photographic light-sensitive Sample No. 9 was prepared.

Layer 1 ... layer containing gelatin at a rate of 1.2 g/m$^2$; blue-sensitive silver chloro-bromide emulsion, 0.32 g/m$^2$ (silver chloride content, 98 mol %); and yellow coupler (Y-1) at a rate of 0.80 g/m$^2$, as dissolved in 0.50 g/m$^2$ of dioctylphthalate Layer 2 ... intermediate layer comprising gelatin at a rate of 0.70 g/m$^2$; anti-irradiation dye (AI-1), 8 mg/m$^2$; and anti-irradiation dye (AI-2), 4 mg/m$^2$ Layer 3 ... layer containing gelatin at a rate of 1.25 g/m$^2$; green-sensitive silver chloro-bromide emulsion, 0.20 g/m$^2$ (silver chloride content, 99 mol %); and magenta coupler (M-1) at a rate of 0.62 g/m$^2$, as dissolved in 0.30 g/m$^2$ of dioctylphthalate Layer 4 ... intermediate layer comprising gelatin at a rate of 1.20 g/m$^2$ Layer 5 ... layer containing gelatin at a rate of 1.20 g/m$^2$; red-sensitive silver chloro-bromide emulsion, 0.30 g/m² (silver chloride content, 99 mol %); and comparative cyan coupler (CC-1) at a rate of 0.45 g/m², as dissolved in 0.20 g/m² of dioctylphthalate Layer 6 ... layer containing gelatin at a rate of 1.00 g/m²; and ultraviolet absorbent (UV-1) at a rate of 0.30 g/m², as dissolved in 0.20 g/m² of dioctylphthalate Layer 7 ... layer comprising gelatin at a rate of 0.50 g/m²

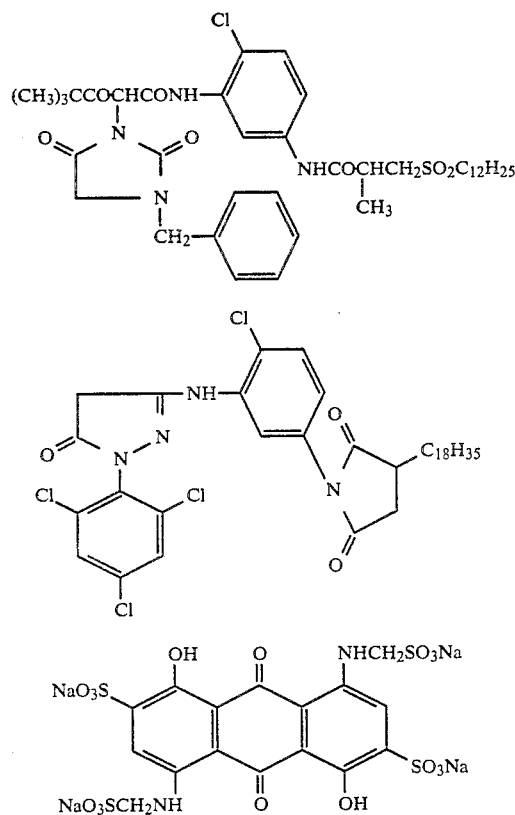

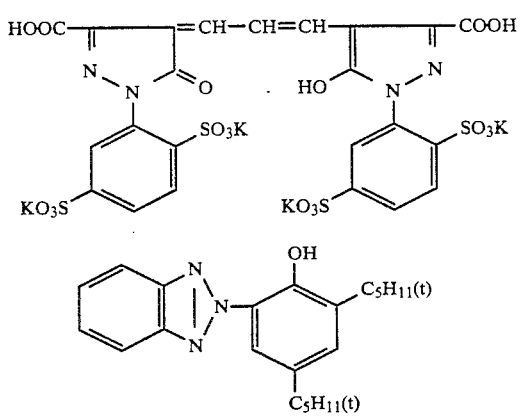

Sodium 2,4-dichloro-6-hydroxy-s-triazine was added as a hardener at a rate of 0.017 g per gram gelatin to Layers 2, 4, and 7.

Sample Nos. 14 through 23 were prepared in a manner identical with that of Sample No. 13 above, except that comparative cyan coupler (CC-1) in Layer 5 of Sample No. 13 was replaced, as specified in Table 2, with each of the cyan couplers of the invention. Each of these cyan couplers was used in mols equivalent to that of cyan coupler (CC-1).

Sample Nos. 13 through 23 were exposed through an optical wedge, thereafter, were subjected to a developing process identical with that of Example 1.

Each sample undergone developing was subjected to sensitometric evaluation, thereby maximum density (Dmax) and sensitivity of a red-sensitive emulsion layer were determined.

Samples undergone the respective treatment above were stored for two weeks under high temperature, high humidity conditions of 80° C. and 90% RH, thereby preservability of cyan dye images (dark fading) was evaluated.

The so-obtained results are listed in Table 2.

TABLE 2

| Sample No. | Coupler | Sensitivity[*1] | Dmax | Image preservability[*2] |
|---|---|---|---|---|
| 1 (Comparative) | CC-1 | 100 | 2.13 | 0.75 |
| 14 (Invention) | Example compound 2 | 101 | 2.20 | 0.84 |
| 15 (Invention) | Example compound 3 | 102 | 2.10 | 0.82 |
| 16 (Invention) | Example compound 10 | 104 | 2.13 | 0.85 |
| 17 (Invention) | Example compound 20 | 102 | 2.20 | 0.80 |
| 18 (Invention) | Example compound 21 | 103 | 2.21 | 0.85 |
| 19 (Invention) | Example compound 8 | 108 | 2.15 | 0.80 |
| 20 (Invention) | Example compound 15 | 107 | 2.30 | 0.90 |
| 21 (Invention) | Example compound 13 | 115 | 2.43 | 0.95 |
| 22 (Invention) | Example compound 14 | 113 | 2.45 | 0.95 |
| 23 (Invention) | Example compound 12 | 108 | 2.20 | 0.82 |

[*1] Relative value based on the sensitivity of Sample No. 13, i.e. 100
[*2] Degraded density of an area whose initial density being 1.0

As apparent from the results in Table 2, the effects of the invention are manifest, too with multilayer silver halide color photographic light-sensitive materials.

At the same time, a color checker (Macbeth) was photographed onto a Sakura Color Sr-V100 (Konica Corporation), and the film was subjected to developing. Then the megative image of the Macbeth color checker was printed onto each of Sample Nos. 13 through 23 mentioned above, so as to adjust the tone of the gray areas thereby hues on each print were compared with those on the color checker. These color papers were processed in a manner same as Example 1.

Samples having a coupler of the invention are especially effective in that blue component is distinguished from cyan component, and that green component exhibits greatly improved brightness. These improvements are attributable to insignificance of the secondary absorption, that is the advantage of a colored dye derived from a coupler of the invention.

EXAMPLE 3

On a paper support same as that of Example 2 were sequentially formed the following layers by coating to prepare a multilayer silver halide color photographic light-sensitive Sample No. 24.

Layer 1 ... layer containing gelatin at a rate of 1.2 g/m²; blue-sensitive silver chloro-bromide emulsion (silver chloride content, 20 mol %), 0.32 g/m² (silver converted value, hereunder applicable); and yellow coupler (Y-2) at a rate of 0.80 g/m², as dissolved in 0.50 g/m² of dioctylphthalate Layer 2 ... intermediate layer comprising gelatin at a rate of 0.70 g/m²; anti-irradiation dye (AI-1), 12 mg/m²; and anti-irradiation dye (AI-2), 6 mg/m²

Layer 3 ... layer containing gelatin at a rate of 1.25 g/m²; green-sensitive silver chloro-bromide emulsion (silver chloride content, 30 mol %), 0.25 g/m²; and magenta coupler (M-1) at a rate of 0.62 g/m², as dissolved in 0.30 g/m² of dioctylphthalate Layer 4 ... intermediate layer comprising gelatin at a rate of 1.20 g/m²

Layer 5 ... layer containing gelatin at a rate of 1.20 g/m²; red-sensitive silver chloro-bromide emulsion (silver chloride content, 30 mol %), 0.30 g/m²; and comparative cyan coupler (CC-1), 0.45 g/m², as dissolved in 0.20 g/m² of dioctylphthalate Layer 6 ... layer containing gelatin at a rate of 100 g/m²; and ultraviolet absorbent (UV-1) at a rate of 0.30 g/m², as dissolved in 0.20 g/m² of dioctylphthalate.

Layer 7 ... layer containing gelatin at a rate of 0.50 g/m²

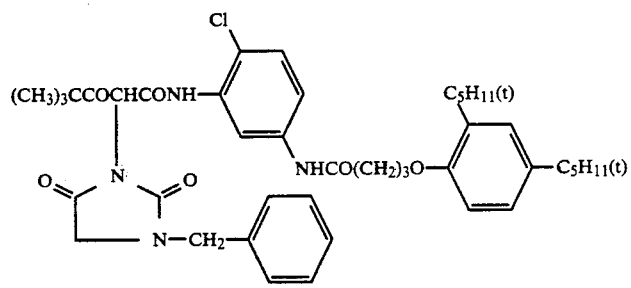

Y-2

Sodium 2,4-dichloro-6-hydroxy-s-triazine was added as a hardener at a rate of 0.017 g per gram gelatin to Layers 2, 4, and 7.

Sample Nos. 25 through 34 were prepared in a manner identical with that of Sample No. 24 above, except that CC-1 of Sample No. 24 was replaced with equivalent mols of a cyan coupler of the invention.

Sample Nos. 24 through 34 were respectively exposed through an optical wedge, and then, were processed as specified below.

| Treatment Procedure (38° C.) | |
|---|---|
| Color developing | 3 min. 30 sec. |
| Bleach-fixing | 1 min. 30 sec. |
| Washing | 1 min. |
| Drying  60~80° C. | 2 min. |

The composition of each processing solution was as follows:

| Color-developer | |
|---|---|
| Water | 800 ml |
| Benzyl alcohol | 15 ml |
| Hydroxylamine sulfate | 2.0 g |
| Potassium bromide | 1.5 g |
| Sodium chloride | 1.0 g |
| Potassium sulfite | 2.0 g |
| Triethanolamine | 2.0 g |
| N-ethyl-N-β-methanesulfonamidoethyl-3-methyl-4-aminaniline sulfate | 4.5 g |
| 1-hydroxyethyledene-1,1-diphosphate (60% aqueous solution) | 1.5 ml |
| Potassium carbonate | 32 g |
| Whitex BB (50% aqueous solution) | 2 ml |

| Color-developer -continued | |
|---|---|
| (Optical brightening agent, Sumitomo Chemical Co., Ltd.) | |

Water was added to prepare one liter solution, that was adjusted to pH=10.0 with 20% potassium hydroxide or 10% dilute sulfuric acid.

| Bleach-fixer | |
|---|---|
| Water | 550 ml |
| Ferric ammonium ethylenediaminetetraacetate | 65 g |
| Ammonium thiosulfate | 85 g |
| Sodium hydrogen sulfite | 10 g |
| Sodium metabisulfite | 2 g |
| Disodium ethylenediaminetetraacetate | 20 g |
| Sodium bromide | 10 g |

Water was added to prepare one liter solution, that was adjusted to pH=7.0 with aqueous ammonium or dilute sulfuric acid.

Each of the so-processed samples was subjected to sensitometry as in Example 2, thereby the Dmax and sensitivity of a red-sensitive emulsion layer were determined.

The preservability of cyan dye image (dark fading property) of each sample that was stored under the conditions identical with those of Example 2 was measured. The results are also listed in Table 3.

TABLE 3

| Sample No. | Coupler | Sensi-tivity[1] | Dmax | Image preserva-bility[2] |
|---|---|---|---|---|
| 24 (Comparative) | CC-1 | 100 | 2.20 | 0.78 |
| 25 (Invention) | Example compound 2 | 108 | 2.23 | 0.83 |
| 26 (Invention) | Example compound 3 | 108 | 2.20 | 0.85 |
| 27 (Invention) | Example compound 10 | 110 | 2.33 | 0.88 |
| 28 (Invention) | Example compound 20 | 113 | 2.35 | 0.89 |
| 29 (Invention) | Example compound 21 | 110 | 2.33 | 0.87 |
| 30 (Invention) | Example compound 8 | 115 | 2.30 | 0.88 |
| 31 (Invention) | Example compound 15 | 115 | 2.40 | 0.95 |
| 32 (Invention) | Example compound 13 | 120 | 2.45 | 0.97 |
| 33 (Invention) | Example compound 14 | 115 | 2.40 | 0.98 |
| 34 (Invention) | Example compound 12 | 113 | 2.25 | 0.90 |

[1] Relative value based on the sensitivity of Sample No. 24, i.e. 100
[2] Post degradation density of an area whose initial density being 1.0

Like the results in Example 2, the results of Example 3 indicate that the samples of the invention excel in dark fading property. Additionally, by photographying a color checker (Macbeth) with a Sakura Color SR-V (Konica Corporation), a negative film was obtained. Then, the negative image of the Macbeth color checker was printed onto each of Sample Nos. 24 through 34 mentioned above, so as to adjust the tone of the gray areas and the samples were subjected to developing, thereby hues on each print were compared with those on the color checker. Samples having a coupler of the invention are especially effective in that blue component is clearly distinguished from cyan component, and that red and green components exhibit greatly improved brightness.

EXAMPLE 4

A core/shell silver iodo-bromide emulsion was prepared according to a method described in Japanese Patent Application No. 31330/1986, wherein the silver halide grains were core/shell type grains having multi-shell structure independently comprising a high iodide content, inter-grain shell that was coated with lamination of shells with iodide contents being gradually smaller toward the outer shells. This emulsion was chemically sensitized with a conventional process, thereby various additives were added to prepare coating solutions of the respective layers, and the coating solutions were applied sequentially on a support made of a triacetyl cellulose film to prepare a color photographic material comprising 13 layers (Sample No. 35).

| | |
|---|---|
| 1st layer; anti-halation layer | |
| Gelatin layer containing black colloidal silver | |
| Gelatin | 2.2 g/m$^2$ |
| 2nd layer; intermediate layer | |
| Gelatin layer containing | |
| emulsificated-dispersion of | |
| 2,5-di-t-octylhydroquinone | |
| Gelatin | 1.2 g/m$^2$ |
| 3rd layer; low sensitivity red-sensitive silver halide emulsion layer | |
| Monodispersed emulsion (Emulsion I) comprising octahedral silver iodo-bromide grains of average size of 0.38 μm, and average iodide content of 7.84% (weight ratio) | |
| Coating silver weight | 1.8 g/m$^2$ |
| Sensitizing dye I | 6 × 10$^{-5}$ mol per mol silver |
| Sensitizing dye II | 1.0 × 10$^{-5}$ mol per mol silver |
| Sensitizing dye III | 1.0 × 10$^{-5}$ mol per mol silver |
| Cyan coupler (CC-2) | 0.06 mol per mol silver |
| Colored cyan coupler (CC-3) | 0.003 mol per mol silver |
| DIR compound (D-1) | 0.0015 mol per mol silver |
| DIR compound (D-2) | 0.002 mol per mol silver |
| Gelatin | 1.4 g/m$^2$ |
| 4th layer; high sensitivity red-sensitive silver halide emulsion layer | |
| Monodispersed emulsion (Emulsion II) comprising octahedral silver iodo-bromide grains of average size of 0.65 μm, and average iodide content of 7.37% (weight ratio) | |
| Coating silver weight | 1.3 g/m$^2$ |
| Sensitizing dye I | 3 × 10$^{-5}$ mol per mol silver |
| Sensitizing dye II | 1.0 × 10$^{-5}$ mol per mol silver |
| Sensitizing dye III | 1.0 × 10$^{-5}$ mol per mol silver |
| Cyan coupler (CC-2) | 0.02 mol per mol silver |
| Colored cyan coupler (CC-3) | 0.0015 mol per mol silver |
| DIR compound (D-2) | 0.001 mol per mol silver |

-continued

| | |
|---|---|
| Gelatin | 1.0 g/m$^2$ |
| 5th layer; intermediate layer | |
| Gelatin layer identical with 2nd layer | |
| Gelatin | 1.0 g/m$^2$ |
| 6th layer; low sensitivity green-sensitive silver halide emulsion layer | |
| Emulsion I; coating silver weight | 1.5 g/m$^2$ |
| Sensitizing dye IV | 2.5 × 10$^{-5}$ mol per mol silver |
| Sensitizing dye V | 1.2 × 10$^{-5}$ mol per mol silver |
| Sensitizing dye VI | 1.0 × 10$^{-5}$ mol per mol silver |
| Magenta coupler (M-2) | 0.05 mol per mol silver |
| Colored magenta coupler (CM-1) | 0.009 mol per mol silver |
| DIR compound (D-1) | 0.0010 mol per mol silver |
| DIR compound (D-3) | 0.0030 mol per mol silver |
| Gelatin | 2.0 g/m$^2$ |
| 7th layer; high sensitivity green-sensitive silver halide emulsion layer | |
| Emulsion II | coating silver weight, 1.4 g/m$^2$ |
| Sensitizing dye IV | 1.5 × 10$^{-5}$ mol per mol silver |
| Sensitizing dye V | 1.0 × 10$^{-5}$ mol per mol silver |
| Sensitizing dye VI | 7.0 × 10$^{-6}$ mol per mol silver |
| Magenta coupler (M-2) | 0.020 mol per mol silver |
| Colored magenta coupler (CM-1) | 0.002 mol per mol silver |
| DIR compound (D-3) | 0.0010 mol per mol silver |
| Gelatin | 1.8 g/m$^2$ |
| 8th layer; intermediate layer | |
| Gelatin layer identical with 2nd layer | |
| Gelatin | 1.0 g/m$^2$ |
| 9th layer; yellow filter layer | |
| Gelatin layer containing yellow colloidal silver, and emulsificated-dispersion of 2,5-di-t-octylhydroquinone | |
| Gelatin | 1.5 g/m$^2$ |
| 10th layer; low sensitivity blue-sensitive silver halide emulsion layer | |
| Monodispersed emulsion (Emulsion I) | |
| Coating silver weight | 0.9 g/m$^2$ |
| Sensitizing dye VII | 1.3 × 10$^{-5}$ mol per mol silver |
| Yellow coupler (Y-3) | 0.29 mol per mol silver |
| Gelatin | 1.9 g/m$^2$ |
| 11th layer; high sensitivity blue-sensitive silver halide emulsion layer | |
| Monodispersed emulsion (Emulsion II) | |
| Coating silver weight | 0.5 g/m$^2$ |
| Sensitizing dye VII | 1.0 × 10$^{-5}$ mol per mol silver |
| Yellow coupler (Y-3) | 0.08 mol per mol silver |
| DIR compound (D-2) | 0.0015 mol per mol silver |
| Gelatin | 1.6 g/m$^2$ |
| 12th layer; 1st protective layer | |
| Gelatin layer containing: | |
| silver iodo-bromide (AgI, 1 mol %; average grain size, 0.07 μm); | |
| coating silver weight | 0.5 g/m$^2$ and, UV-2 and UV-3 |
| Gelatin | 1.2 g/m$^2$ |
| 13th layer; 2nd protective layer | |
| Gelatin layer containing: | |
| polymethyl methacrylate grains (dia., 1.5 μm) grains of ethyl methacrylate/methyl methacrylate/methacrylic acid copolymer (average grain size, 2.5 μm) | |
| polydimethylsiloxane | 5 mg/m$^2$ |
| C$_8$F$_{17}$SO$_2$NCH$_2$COONa<br>\|<br>C$_2$H$_5$ | 10 mg/m$^2$ |
| and, formalin scavenger (HS-1) | |
| Gelatin | 1.2 g/m$^2$ |

To each of the above layers were added, in addition to the above compositions, gelatin hardener (H-1) and surface active agent.

In addition, by replacing cyan coupler CC-2 in the third and fourth layers with a coupler of the invention specified in Table 4, seven samples were prepared and subjected to coating.

(Additives)
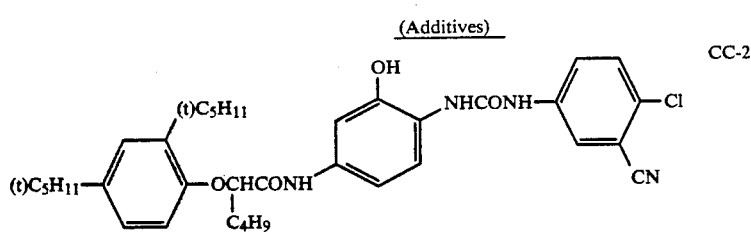
CC-2
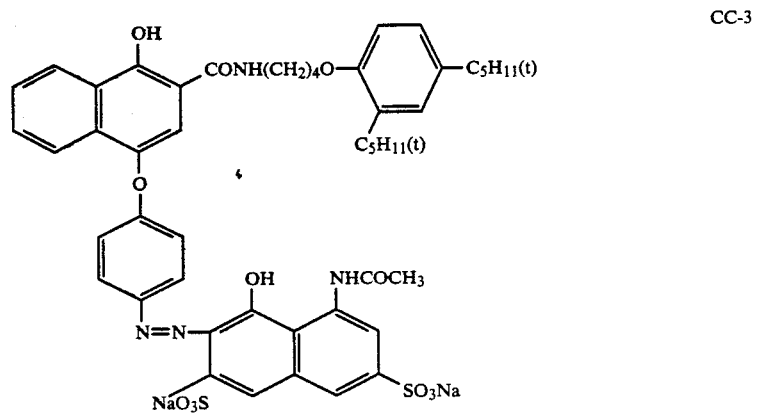
CC-3
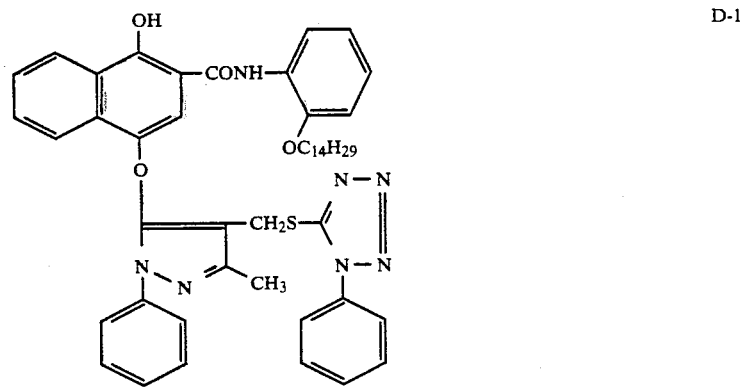
D-1
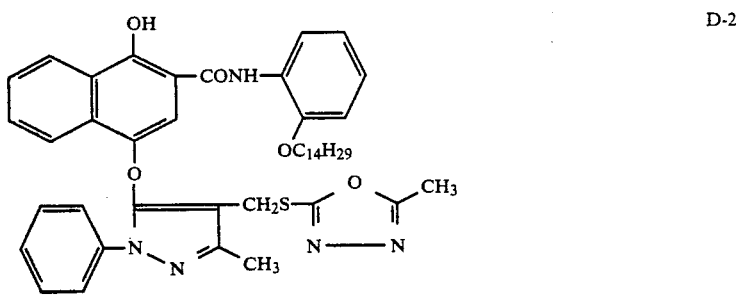
D-2
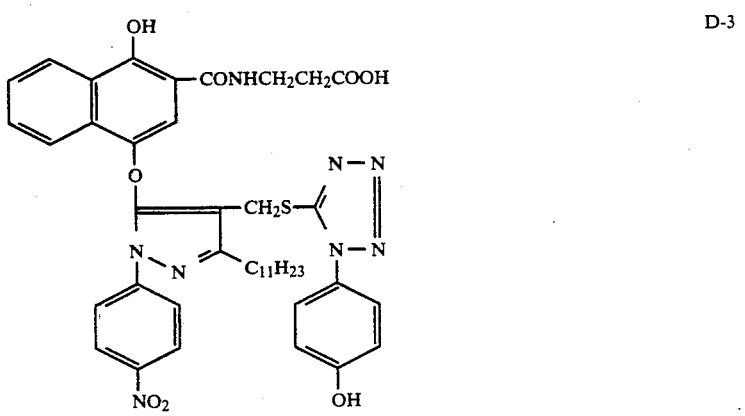
D-3

-continued
(Additives)
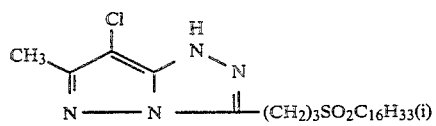
M-2
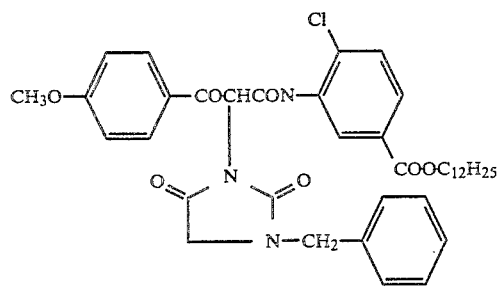
Y-3
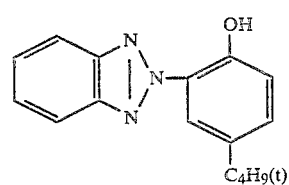
UV-2
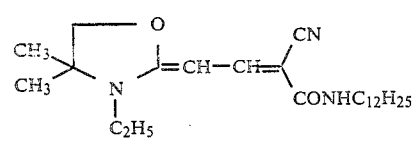
UV-3
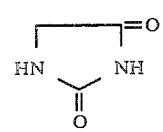
HS-1
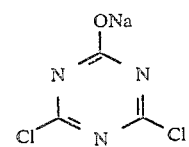
H-1
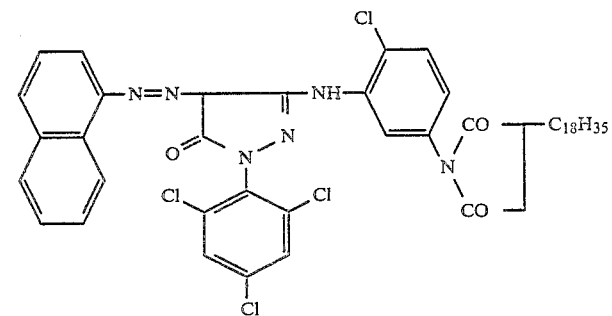
CM-1
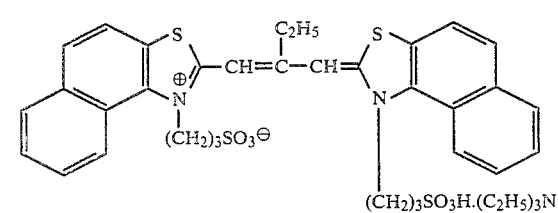
Sensitizing dye I (Additives)

Sensitizing dye II

[structure: bis-benzothiazole with C₂H₅ on central carbon, Cl substituents, (CH₂)₃SO₃⁻ and (CH₂)₃SO₃H groups]

Sensitizing dye III

[structure: benzothiazole-benzoxazole with C₂H₅, Cl substituents, (CH₂)₄SO₃⁻ and (CH₂)₄SO₃H·(C₂H₅)₃N groups]

Sensitizing dye IV

[structure: bis-benzoxazole with phenyl substituents, C₂H₅, (CH₂)₄SO₃⁻ and (CH₂)₄SO₃H·(C₂H₅)₃N groups]

Sensitizing dye V

[structure: bis-naphthoxazole with C₂H₅, (CH₂)₃SO₃⁻ and (CH₂)₃SO₃H·(C₂H₅)₃N groups]

Sensitizing dye VI

[structure: bis-benzoxazole with Cl substituents, (CH₂)₄SO₃⁻ and (CH₂)₄SO₃H·(C₂H₅)₃N groups]

Sensitizing dye VII

[structure: bis-benzothiazole with CH₃O substituents, (CH₂)₃SO₃⁻ and (CH₂)₃SO₃Na groups]

The so-prepared samples were subjected to wedge exposing with white light, and subjected to developing specified below, thereby their sensitivity and fog level were determined. The sensitivity was defined as an inverse of exposure level exhibiting a density level of fog +0.5, and is relative sensitivity based on the sensitivity of Sample No. 35, i.e. 100.

The samples undergone developing were subjected to a preservability test for 20 days under accelerated weathering conditions of 60° C. and 80% RH, thereby heat resistance of each sample was evaluated based on post-deterioration residual image percentage of an area whose initial density being 1.0. The results are also listed in Table 4.

| Treatment Procedure (38° C.) | |
|---|---|
| Color developing | 3 min. 15 sec. |
| Bleaching | 6 min. 30 sec. |
| Washing | 3 min. 15 sec. |
| Fixing | 6 min. 30 sec. |
| Washing | 3 min. 15 sec. |
| Stabilizing | 1 min. 30 sec. |
| Drying | |

The composition of each processing solution used in each processing was as follows:

| Color-developer | |
|---|---|
| 4-amino-3-methyl-N-ethyl-N-(β-hydroxyethyl)-aniline sulfate | 4.75 g |
| Sodium sulfite anhydride | 4.25 g |
| Hydroxylaminie ½ sulfate | 2.0 g |
| Potassium carbonate anhydride | 37.5 g |
| Sodium bromide | 1.3 g |
| Trisodium nitrilotriacetate (monohydrate) | 2.5 g |
| Potassium hydroxide | 1.0 g |

Water was added to prepare one liter solution.

| Bleaching solution | |
|---|---|
| Ferric ammonium ethylenediaminetetraacetate | 100 g |
| Diammonium ethylenediaminetetraacetate | 10.0 g |
| Ammonium bromide | 150.0 g |
| Glacial acetic aci | 0.0 ml |

Water was added to prepare one liter solution, that was adjusted to pH=6.0 with aqueous ammonium.

| Fixer | |
|---|---|
| Ammonium thiosulfate | 175.0 g |
| Sodium sulfite anhydride | 8.5 g |

-continued

| Fixer | |
|---|---|
| Sodium metasulfite | 2.3 g |

Water was added to prepare one liter solution, that was adjusted to pH=6.0 with acetic acid.

| Stabilizer | |
|---|---|
| Formalin (37% aqueous solution) | 1.5 ml |
| Konidax (Konica Corporation) | 7.5 ml |

Water was added to prepare one liter solution.

TABLE 4

| Sample No. | Coupler 3rd | Coupler 4th | Sensitivity | Fog | Image preservability (%) |
|---|---|---|---|---|---|
| 35 | CC-2 | CC-2 | 100 | 0.13 | 96 |
| 36 | CC-2 | Example compound 44 | 120 | 0.12 | 97 |
| 37 | CC-2 | Example compound 20 | 125 | 0.13 | 96 |
| 38 | Example compound 32 | Example compound 21 | 130 | 0.12 | 97 |
| 39 | CC-2 | Example compound 23 | 135 | 0.13 | 96 |
| 40 | CC-2 | Example compound 16 | 142 | 0.13 | 97 |
| 41 | Example compound 15 | Example compound 58 | 145 | 0.11 | 98 |
| 42 | Example compound 59 | Example compound 59 | 145 | 0.12 | 98 |

As can be understood from the results according to the invention, a color negative film incorporating a compound of the invention exhibits high sensitivity, and good image preservability.

EXAMPLE 5

On a triacetyl cellulose film having a subbing layer of maleic acid anhydride/vinyl acetate copolymer were, after backing-antistatic treatment, sequentially formed the layers of the following compositions, to prepare Sample No. 43. An amount added means an amount per mol silver halide unless otherwise specified.

| Backing-antistatic treatment | | |
|---|---|---|
| 1st backing layer: | stearic acid | 20 mg/m$^2$ |
| | diacetyl cellulose | 10 mg/m$^2$ |
| | alumina sol | 1 g/m$^2$ |
| 2nd backing layer: | diacetyl cellulose | 50 mg/m$^2$ |
| | stearic acid | 10 mg/m$^2$ |
| | silica matting agent (average grain size, 3 μm) | 50 mg/m$^2$ |

| Layers on support | |
|---|---|
| 1st layer: | anti-halation layer<br>Ultraviolet absorbent-2, 0.4 g/m$^2$;<br>ultraviolet absorbent-3, 0.3 g/m$^2$;<br>black colloidal silver, 0.24 g/m$^2$;<br>and gelatin, 2.7 g/m$^2$ |
| 2nd layer: | intermediate layer<br>2,5-di-t-octylhydroquinone, 0.1 g/m$^2$; and gelatin, 1.0 g/m$^2$ |
| 3rd layer: | low sensitivity red-sensitive silver halide emulsion layer<br>Monodispersed emulsion (Emulsion III), coating silver weight, 0.5 g/m$^2$, AgBrI grains of average size 0.35 μm, containing 2.5 mol % AgI; sensitizing dye VIII, 7.6 × 10$^{-4}$ mol; coupler CC-4, 0.1 mol, and gelatin, 0.9 g/m$^2$ |
| 4th layer: | high sensitivity red-sensitive silver halide emulsion layer<br>Monodispersed emulsion (Emulsion IV), coating silver weight, 0.8 g/m$^2$, AgBrI grains of average size 0.75 μm, containing 2.5 mol % AgI; sensitizing dye VIII, 3.2 × 10$^{-4}$ mol; coupler CC-4, 0.2 mol, and gelatin 1.75 g/m$^2$ |
| 5th layer: | intermediate layer<br>2,5-di-t-octylhydroquinone, 1.1 g/m$^2$; and gelatin, 0.9 g/m$^2$ |
| 6th layer: | low sensitivity green-sensitive silver halide emulsion layer<br>Emulsion III, coating silver weight, 1.0 g/m$^2$;<br>sensitizing dye IX, 6.6 × 10$^{-4}$ mol; sensitizing dye X, 0.6 × 10$^{-4}$ mol; coupler M-3, 0.05 mol; and gelatin, 0.8 g/m$^2$ |
| 7th layer: | high sensitivity green-sensitive silver halide emulsion layer<br>Emulsion IV, coating silver weight, 1.0 g/m$^2$;<br>sensitizing dye IX, 2.76 × 10$^{-4}$ mol; sensitizing dye X, 0.23 × 10$^{-4}$ mol; coupler M-3, 0.15 mol; and gelatin, 1.5 g/m$^2$ |
| 8th layer: | intermediate layer<br>Same as 5th layer |
| 9th layer: | yellow filter layer<br>Yellow colloidal silver, 0.1 g/m$^2$; gelatin, 0.9 g/m$^2$; and 2,5-di-t-octylhydroquinone, 0.1 g/m$^2$ |
| 10th layer: | low sensitivity blue-sensitive silver halide emulsion layer<br>Monodispersed emulsion (Emulsion V), coating silver weight, 0.4 g/m$^2$, AgBrI grains of average size 0.6 μm, containing 2.5 mol % AgI; spectral sensitizing dye XI, 2.65 × 10$^{-4}$ mol; coupler Y-4, 0.3 mol, and gelatin, 1.3 g/m$^2$ |
| 11th layer: | high sensitivity blue-sensitive silver halide emulsion layer<br>Monodispersed emulsion (Emulsion VI), coating silver weight, 0.8 g/m$^2$, comprising AgBrI grains of average size 1.0 μm, containing 2.5 mol % AgI; spectral sensitizing dye XI, 1.59 × 10$^{-4}$ mol; coupler Y-4, 0.5 mol, and gelatin 2.1 g/m$^2$ |
| 12th layer: | 1st protective layer<br>Ultraviolet absorbent-2, 0.4 g/m$^2$; ultraviolet absorbent-3, 0.3 g/m$^2$; gelatin, 1.2 g/m$^2$; and 2,5-di-t-octylhydroquinone, 0.1 g/m$^2$ |
| 13th layer: | 2nd protective layer<br>Non-light-sensitive, fine grain silver halide emulsion, coating silver weight, 0.3 g/m$^2$, comprising AgBrI grains of average size 0.06 μm, containing 1 mol % AgI; polyethyl methacrylate grains (dia., 1.5 μm); gelatin, 0.7 g/m$^2$; and surface active agent 1 |

Other than the above-mentioned compositions, each layer incorporated gelatin hardener 1 or surface active agent. Tricresyl phosphate was used as a solvent for a coupler.

Every emulsion used was a monodispersed emulsion of octahedral grains, wherein each emulsion was prepared by growing a seed grain emulsion containing grains of 0.095 μm or 0.25 μm (average silver iodide content, 2 mol %) at 45° C. in the presence of ammonium, in compliance with controlled double jet process according to which pAg and PH are controlled. The silver iodide contents in cores, intermediate layers, and shells in grains were varied by changing the composition of halide solution being added.

To grow grains of the core/shell silver halide emulsion, methods disclosed in Japanese Patent O.P.I. Publication Nos. 52238/1984, 138538/1985, 49938/1983, and 122935/1985 were used.

COMPOUNDS USED FOR PREPARING SAMPLES

Ultraviolet absorbent 2

(Same as UV-2 in Example 4)

Ultraviolet absorbent 3

(Same as UV-3 in Example 4)

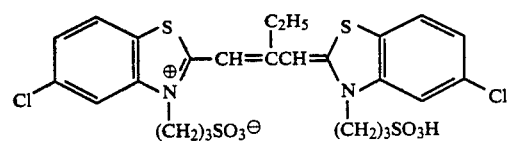

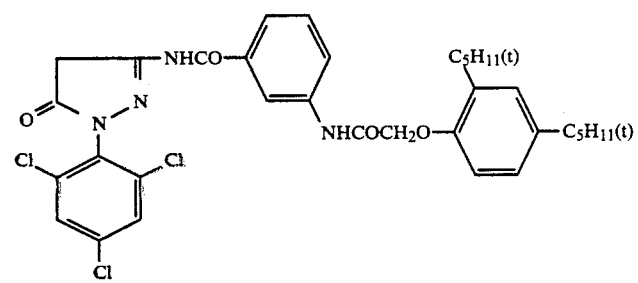

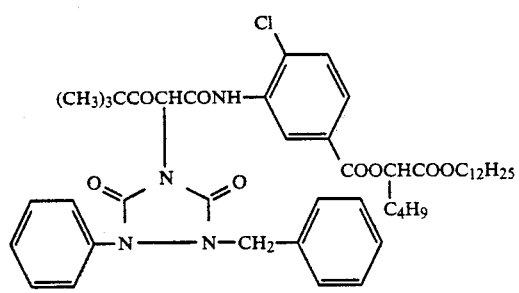

Next, Sample Nos. 44 through 48 were prepared in a manner identical with that of Sample No. 43 except that cyan coupler CC-4 in the third and fourth layers was replaced with a coupler of the invention specified in Table 5, in mols equivalent to coupler CC-4.

Sensitizing dye-IX

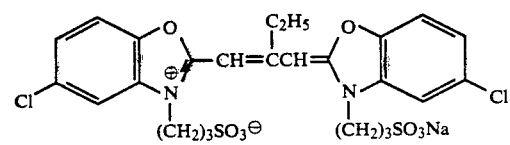

Sensitizing dye-X

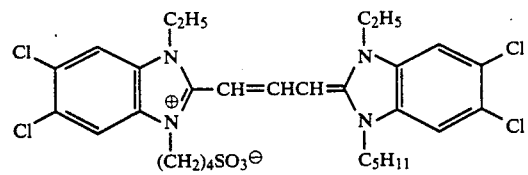

Sensitizing dye-XI

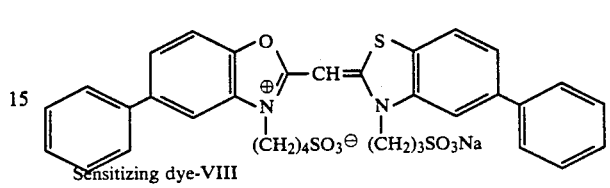

Sensitizing dye-VIII

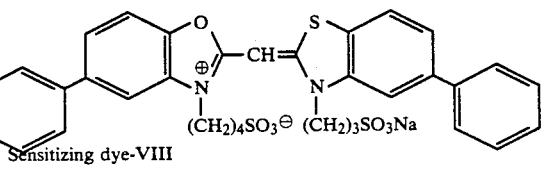

Coupler M-3

Coupler Y-4

Surface active agent 1

Coupler CC-4

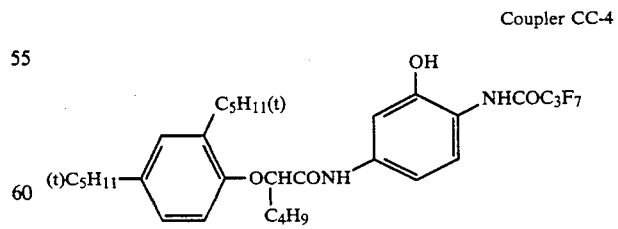

Each sample was subjected to neutral exposing, and then to developing, thereby in accordance with the following reversal processing procedure. Heat resistance of a cyan dye image of each so-processed sample was evaluated (indicated with a residual dye percentage on an area whose initial density being 1.0, wherein each sample was preserved for 20 days under conditions identical with those in Example 3).

| Processing | Processing time | Processing temperature |
|---|---|---|
| Primary developing | 6' | 38° C. (± 0.3) |
| Washing | 2' | 38° C. (± 0.3) |
| Reversal processing | 2' | 38° C. (± 0.3) |
| Color developing | 6' | 38° C. (± 0.3) |
| Adjusting | 2' | 38° C. (± 0.3) |
| Bleaching | 6' | 38° C. (± 0.3) |
| Fixing | 4' | 38° C. (± 0.3) |
| Washing | 4' | 38° C. (± 0.3) |
| Stabilizing | 1' | Normal temperature |
| Drying | | |
| Primary developer | | |
| Sodium tetrapolyphosphate | | 2 g |
| Sodium sulfite | | 20 g |
| Hydroquinone monosulfonic acid | | 30 g |
| Sodium carbonate (monohydrate) | | 30 g |
| 1-phenyl-4-methyl-4-hydroxymethyl-3-pyrazolidone | | 2 g |
| Potassium bromide | | 2.5 g |
| Potassium thiocyanate | | 1.2 g |
| Potassium iodide (0.1% aqueous solution) | | 2 ml |
| Water to | | 1000 ml |
| Reversal processing | | |
| Hexasodium nitrilotrimethylenephosphate | | 3 g |
| Stanous chloride (dihydrate) | | 1 g |
| p-aminophenol | | 0.1 g |
| Sodium hydroxide | | 8 g |
| Glacial acetic acid | | 15 ml |
| Water to | | 1000 ml |
| Color developer | | |
| Sodium tetrapolyphosphate | | 2 g |
| Sodium sulfite | | 7 g |
| Sodium tertiary phosphate (dihydrate) | | 36 g |
| Potassium bromide | | 1 g |
| Potassium iodide (0.1% aqueous solution) | | 90 ml |
| Sodium hydroxide | | 3 g |
| Citrazinic acid | | 1.5 g |
| N-methyl-N-(β-methanesulfonamidoethyl)-3-methyl-4-aminoaniline sulfate | | 11 g |
| Ethylenediamine | | 3 g |
| Water to | | 1000 ml |
| Adjusting solution | | |
| Sodium sulfite | | 12 g |
| Sodium ethylenediaminetetraacetate (dihydrate) | | 8 g |
| Thioglyceline | | 0.4 ml |
| Glacial acetic acid | | 3 ml |
| Water to | | 1000 ml |
| Bleaching solution | | |
| Sodium ethylenediaminetetraacetate (dihydrate) | | 2.0 g |
| Ferric ammonium ethylenediaminetetraacetate (dihydrate) | | 120.0 g |
| Potassium bromide | | 100.0 g |
| Water to | | 1000 ml |
| Fixer | | |
| Ammonium thiosulfate | | 80.0 g |
| Sodium sulfite | | 5.0 g |
| Sodium bisulfite | | 5.0 g |
| Water to | | 1000 ml |
| Stabilizer | | |
| Formalin (37 wt %) | | 5.0 ml |
| Konidax (Konica Corporation) | | 5.0 ml |
| Water to | | 1000 ml |

The results are listed in Table 5.

TABLE 5

| Sample No. | Coupler | Dmax | Heat resistance |
|---|---|---|---|
| 43 (Comparative) | CC-4 | 3.20 | 90% |
| 44 (Invention) | Example compound 3 | 3.20 | 97 |
| 45 (Invention) | Example compound 9 | 3.30 | 98 |
| 46 (Invention) | Example compound 5 | 3.00 | 95 |
| 47 (Invention) | Example compound 62 | 3.25 | 97 |
| 48 (Invention) | Example compound 36 | 3.10 | 96 |
| 49 (Invention) | Example compound 49 | 3.15 | 95 |
| 50 (Invention) | Example compound 55 | 3.20 | 96 |

As can be understood from the results in Table 5, even in the reversal processing, a coupler of the invention is capable of forming a cyan dye image of good heat resistance.

Additionally, samples prepared by developing photographs of a color checker (Macbeth), that were obtained using Sample Nos. 43 through 50, were visually evaluated for color reproducibility, whereby compared with the comparative sample, sample of the invention exhibited significant improvement both in separation of blue component from cyan component, and color reproduction of green and red colors.

What is claimed is:

1. A light-sensitive silver halide photographic material comprising a support having thereon at least one silver halide emulsion layer containing a cyan coupler represented by the following formula:

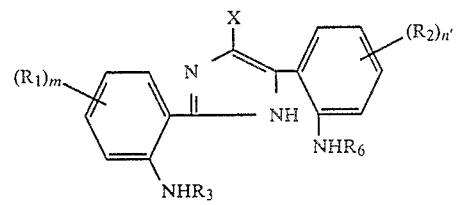

wherein $R_1$ and $R_2$ each represent a substituent; $R_3$ and $R_6$ each represent a —$COR_4$ group, a —$COOR_4$ group, or an —$SO_2R_4$ group in which $R_4$ represents an alkyl group, an aryl group, or a heterocyclic group, X represents a hydrogen atom or a group capable of being split off upon reaction with the oxidized product of a color developing agent; m represents an integer of from 0 to 4; and n' represents an integer of from 0 to 4.

2. The material of claim 1 wherein said silver halide emulsion layer is a red-sensitive silver halide emulsion layer.

3. The material of claim 1, wherein said cyan coupler is added to said silver halide emulsion layer in an amount of from $2 \times 10^{-3}$ mol to $8 \times 10^{-1}$ mol per mol silver halide.

4. The material of claim 3, wherein said cyan coupler is added to said silver halide emulsion layer in an amount of from $1 \times 10^{-2}$ mol to $5 \times 10^{-1}$ mol per mol silver halide.

5. The material of claim 1, wherein silver halide grains contained in said silver halide emulsion layer comprise not less than 90 mol % of silver chloride.

6. The material of claim 5, wherein said silver halide grains contain not more than 5 mol % of silver bromide and not more than 0.5 mol % of silver iodide.

7. The material of claim 6, wherein said silver halide grains comprise silver chlorobromide containing silver bromide in an amount of from 0.1 to 1.0 mol %.

* * * * *